United States Patent
Mineo (10) Patent No.: US 10,576,511 B2
(45) Date of Patent: Mar. 3, 2020

(54) AUTOMATIC CLEANING VALIDATION SWABBING DEVICES, METHODS, AND SYSTEMS

(71) Applicant: Encova Consulting, Inc., Cary, NC (US)

(72) Inventor: Richard A. Mineo, Cary, NC (US)

(*) Notice: Subject to any disclaimer, the term of this patent is extended or adjusted under 35 U.S.C. 154(b) by 0 days.

(21) Appl. No.: 15/799,144

(22) Filed: Oct. 31, 2017

(65) Prior Publication Data

US 2018/0100786 A1    Apr. 12, 2018

Related U.S. Application Data

(62) Division of application No. 14/764,996, filed on Jul. 31, 2015.

(51) Int. Cl.
| | | |
|---|---|---|
| *B08B 9/46* | (2006.01) | |
| *G01N 1/02* | (2006.01) | |
| *B08B 1/00* | (2006.01) | |

(52) U.S. Cl.
CPC ............ *B08B 9/46* (2013.01); *G01N 1/02* (2013.01); *B08B 1/008* (2013.01); *G01N 2001/028* (2013.01)

(58) Field of Classification Search
CPC B08B 1/003; B08B 1/008; B08B 9/08; B08B 9/0804; B08B 9/0808; B08B 9/087; B08B 9/46; G01N 1/02; G01N 1/022; G01N 1/024; G01N 1/025; G01N 1/027; G01N 2001/028; G01T 7/02
See application file for complete search history.

(56) References Cited

U.S. PATENT DOCUMENTS

| | | | | |
|---|---|---|---|---|
| 5,823,592 | A * | 10/1998 | Kalidindi | B25J 1/04 294/24 |
| 6,207,406 | B1 * | 3/2001 | Wilkins | C12Q 1/24 435/30 |
| 6,318,192 | B1 * | 11/2001 | Carbone | G01N 1/04 73/863.81 |
| 8,011,258 | B2 * | 9/2011 | Fine | G01N 1/02 73/864.71 |
| 2013/0213154 | A1 * | 8/2013 | Crowder | B08B 1/00 73/865.8 |

\* cited by examiner

*Primary Examiner* — Justin N Olamit
(74) *Attorney, Agent, or Firm* — O'Connor & Company; Ryan P. O'Connor (57) ABSTRACT

In some variations, this invention provides an electro-mechanical device for automated cleaning validation of a selected surface. The device moves a wetted swab over a cleaned surface to recover any remaining soil left over from the cleaning process. The device accepts a standard sampling swab that has been wetted with the required liquid solution. The device maintains constant swab pressure to ensure maximum recovery of soil or contaminants. The device includes an electronic controller for adjusting the movement of parts to effectively validate cleaning of the selected surface. The surface to be validated may be a substantially flat surface, or rounded. The surface may be contained within a vessel, reactor, a pipe, tank, or other equipment. The device may be disposed on an extension arm to allow the device to be positioned appropriately, without the need for a person to be close to the device for validation.

4 Claims, 6 Drawing Sheets

AUTOMATIC CLEANING VALIDATION SWABBING DEVICES, METHODS, AND SYSTEMS

PRIORITY DATA

This patent application is a divisional of U.S. patent application Ser. No. 14/746,996, filed on Jul. 31, 2015, which is a U.S. national-stage patent application under the Patent Cooperation Treaty of PCT/US2013/073362, filed on Dec. 5, 2013, which claims priority to U.S. Provisional Patent App. No. 61/734,723, filed on Dec. 7, 2012, each of which is hereby incorporated by reference herein.

FIELD OF THE INVENTION

The present invention generally relates to automated validation of surface cleanliness in biotechnology, pharmaceutical, medical-device, and related industries.

BACKGROUND OF THE INVENTION

In biotechnology, pharmaceutical, medical-device, and related industries, cleanliness of surfaces and equipment is a critical issue. It can be very difficult to ascertain whether a proper amount of cleaning has been performed and/or maintained.

One current problem with cleaning validation sampling is human error and inconsistent execution. This issue is most seen in hard to reach areas such as inside tanks or vessels. Companies spend considerable amounts of time and money training and certifying individuals to perform swabbing. Even with a lot of training there is no guarantee that the sample will not yield a false passing result, since not enough surface was swabbed or they did not apply the correct amount of pressure. Even with the use of highly trained validation specialists, there is a significant risk of generating false positive or negative results due to variability in a number of factors including but not limited to actual swabbed surface area or actual pressure applied to the surface.

Confined space entry to perform swabbing is dangerous. Multiple people are needed (three minimum) to ensure the safety of the person swabbing the vessel. If swabbing is performed by use of a telescoping pole as opposed to vessel entry, then the risk of not properly performing the sampling increases due to the distance between the person controlling the swab and the swab location.

SUMMARY OF THE INVENTION

In some variations, this invention provides an electro-mechanical device for automated cleaning validation of a selected surface, the device comprising:
(a) an outer frame that defines a selected sampling area disposed within the outer frame, wherein the selected sampling area is contained within the selected surface;
(b) a horizontally movable inner shaft extending inward from the outer frame;
(c) an adjustable housing connected to the inner shaft, wherein the adjustable housing is configured with a vertically movable and rotatable dry or wetted swab capable of recovering residual contaminants on the selected surface; and
(d) an electronic controller for controlling the vertically movable and rotatable swab to validate cleaning of the selected surface.

Preferably, the frame is fabricated from a material (such as stainless steel) that does not contaminate the swab or the surface. In some embodiments, the shape of the frame is square, rectangular, circular, for example. In some embodiments, the selected sampling area is from 1 square inch to 10 square inches, such as about 4 square inches. The swab is typically a disposable swab, although a cleanable and reusable swab may be used instead.

The horizontally movable inner shaft may be connected to a screw drive or may be movable by hydraulics. The adjustable housing is preferably configured to maintain a substantially constant surface pressure of the swab. A substantially constant surface pressure may be maintained with a spring, for example. In some embodiments, the adjustable housing includes a magnet for vertically moving the swab. The adjustable housing may include a gear or hydraulics for rotating the swab.

The electronic controller may be programmed to move the swab over a pre-defined pattern within the selected sampling area. For example, the pre-defined pattern may include two sequential patterns defining a first and second phase of movement of the swab. In some embodiments, movement of the swab in the first phase is perpendicular (with respect to the surface) to movement of the swab in the second phase.

The surface to be validated may be a substantially flat surface, or rounded (such as when the surface is contained in a pipe or tube). The surface may be contained within a vessel, reactor, a pipe, tank, or other equipment. The device may be disposed on an extension arm to allow the device to be positioned appropriately, without the need for a person to be close to the device for validation. This can aid in safety, since a human does not need to enter a vessel, reactor, or pipe, for example.

In some variations, an electro-mechanical device is provided for automated cleaning validation of a selected sampling area within a pipe or vessel (or tube, or other cylindrical member), comprising:
(a) an axial shaft extending axially within open volume of a pipe or vessel;
(b) a radial shaft, disposed perpendicular with the axial shaft, extending radially toward a surface of the pipe or vessel;
(c) an adjustable housing connected to the radial shaft, wherein the adjustable housing is configured with a movable and rotatable wetted swab capable of recovering residual contaminants on the selected sampling area; and
(d) an electronic controller for controlling the movable and rotatable swab to validate cleaning of the selected sampling area.

In some embodiments, the selected sampling area is from 1 square inch to 10 square inches on the inner or outer surface of a pipe, tube, or other cylindrical member. The adjustable housing may be configured (such as with a spring or other known means) to maintain a substantially constant surface pressure of the swab. The swab is a disposable swab, in preferred embodiments. The electronic controller is programmed to move the swab over a pre-defined pattern within the selected sampling area, in certain embodiments of the invention.

The present invention also provides an automated method of cleaning validation of a selected surface, the method comprising:
(a) selecting a sampling area contained within a selected surface to be validated for proper cleaning;
(b) disposing a device onto the sampling area, wherein the device comprises an adjustable housing configured with a movable and rotatable wetted swab;

(c) moving the swab over the sampling area to recover residual contaminants;

(d) measuring or testing the residual contaminants recovered during step (c); and (e) based on measurements or tests obtained in step (d), indicating whether or not the selected surface was properly cleaned prior to step (a).

Certain devices of the invention, or methods of use, are shown in FIGS. 1-6, which are exemplary and not intended to restrict the scope herein. Also, the present invention provides systems which include devices as disclosed and/or are configured to carry out methods as disclosed.

These and other embodiments, features, and advantages of the present invention will become more apparent to those skilled in the art when taken with reference to the following detailed description of the invention.

DETAILED DESCRIPTION OF EMBODIMENTS OF THE INVENTION

Certain embodiments of the present invention will now be further described in more detail, in a manner that enables the claimed invention so that a person of ordinary skill in this art can make and use the present invention.

Unless otherwise indicated, all numbers expressing reaction conditions, concentrations, yields, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. If a definition set forth in this section is contrary to or otherwise inconsistent with a definition set forth in patents, published patent applications, and other publications that are incorporated by reference, the definition set forth in this specification prevails over the definition that is incorporated herein by reference.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

In some variations, this invention provides an electromechanical device for automated cleaning validation of a selected surface, the device comprising:

(a) an outer frame that defines a selected sampling area disposed within the outer frame, wherein the selected sampling area is contained within the selected surface;

(b) a horizontally movable inner shaft extending inward from the outer frame;

(c) an adjustable housing connected to the inner shaft, wherein the adjustable housing is configured with a vertically movable and rotatable dry or wetted swab capable of recovering residual contaminants on the selected surface; and (d) an electronic controller for controlling the vertically movable and rotatable swab to validate cleaning of the selected surface.

Preferably, the frame is fabricated from a material (such as stainless steel) that does not contaminate the swab or the surface. In some embodiments, the shape of the frame is square, rectangular, circular, for example. In some embodiments, the selected sampling area is from 1 square inch to 10 square inches, such as about 4 square inches.

The swab is typically a disposable swab, although a cleanable and reusable swab may be used instead. Also, the frame contact surface may be disposable, such as with a disposable protective guard or cover. In some embodiments, a sanitization step may be carried out to ensure that the device is clean.

The horizontally movable inner shaft may be connected to a screw drive or may be movable by hydraulics. The adjustable housing is preferably configured to maintain a substantially constant surface pressure of the swab. A substantially constant surface pressure may be maintained with a spring, for example. In some embodiments, the adjustable housing includes a magnet for vertically moving the swab. The adjustable housing may include a gear or hydraulics for rotating the swab.

The electronic controller may be programmed to move the swab over a pre-defined pattern within the selected sampling area. For example, the pre-defined pattern may include two sequential patterns defining a first and second phase of movement of the swab. In some embodiments, movement of the swab in the first phase is perpendicular (with respect to the surface) to movement of the swab in the second phase.

The surface to be validated may be a substantially flat surface, or rounded (such as when the surface is contained in a pipe or tube). The surface may be contained within a vessel, reactor, a pipe, tank, or other equipment. The device may be disposed on an extension arm to allow the device to be positioned appropriately, without the need for a person to be close to the device for validation. This can aid in safety, since a human does not need to enter a vessel, reactor, or pipe, for example.

In some variations, an electro-mechanical device is provided for automated cleaning validation of a selected sampling area within a pipe or vessel (or tube, or other cylindrical member), comprising:

(a) an axial shaft extending axially within open volume of a pipe or vessel;

(b) a radial shaft, disposed perpendicular with the axial shaft, extending radially toward a surface of the pipe or vessel;

(c) an adjustable housing connected to the radial shaft, wherein the adjustable housing is configured with a movable and rotatable wetted swab capable of recovering residual contaminants on the selected sampling area; and (d) an electronic controller for controlling the movable and rotatable swab to validate cleaning of the selected sampling area.

In some embodiments, the selected sampling area is from 1 square inch to 10 square inches on the inner or outer surface of a pipe, tube, or other cylindrical member. The adjustable housing may be configured (such as with a spring or other known means) to maintain a substantially constant surface pressure of the swab. The swab is a disposable swab, in preferred embodiments. The electronic controller is programmed to move the swab over a pre-defined pattern within the selected sampling area, in certain embodiments of the invention.

The present invention also provides an automated method of cleaning validation of a selected surface, the method comprising:

(a) selecting a sampling area contained within a selected surface to be validated for proper cleaning;

(b) disposing a device onto the sampling area, wherein the device comprises an adjustable housing configured with a movable and rotatable wetted swab;

(c) moving the swab over the sampling area to recover residual contaminants;

(d) measuring or testing the residual contaminants recovered during step (c); and (e) based on measurements or tests obtained in step (d), indicating whether or not the selected surface was properly cleaned prior to step (a).

Some embodiments will be described with reference to FIGS. 1-6, which by no means should be construed as limiting the scope of the invention.

Figure 1:
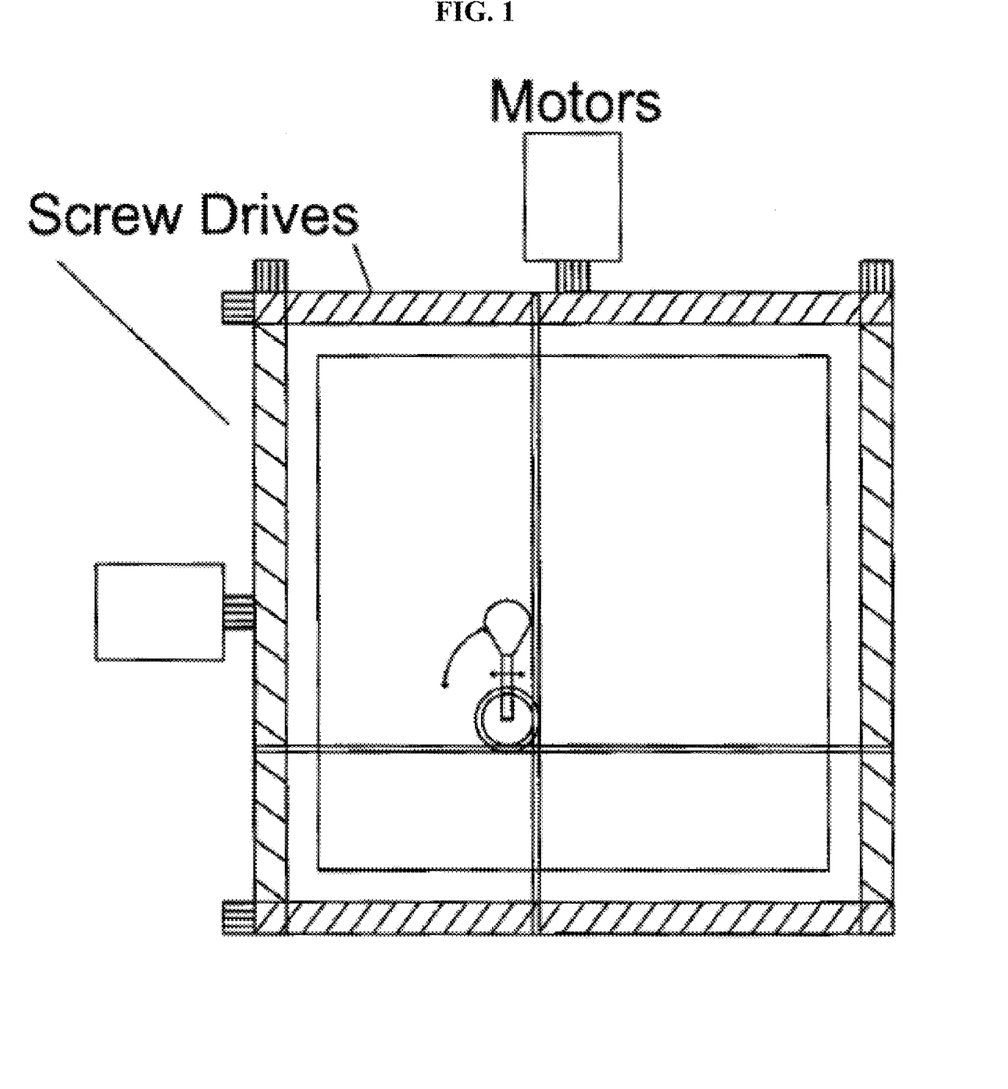
FIG. 1 is a device schematic according to some embodiments of the invention.
Figure 2:
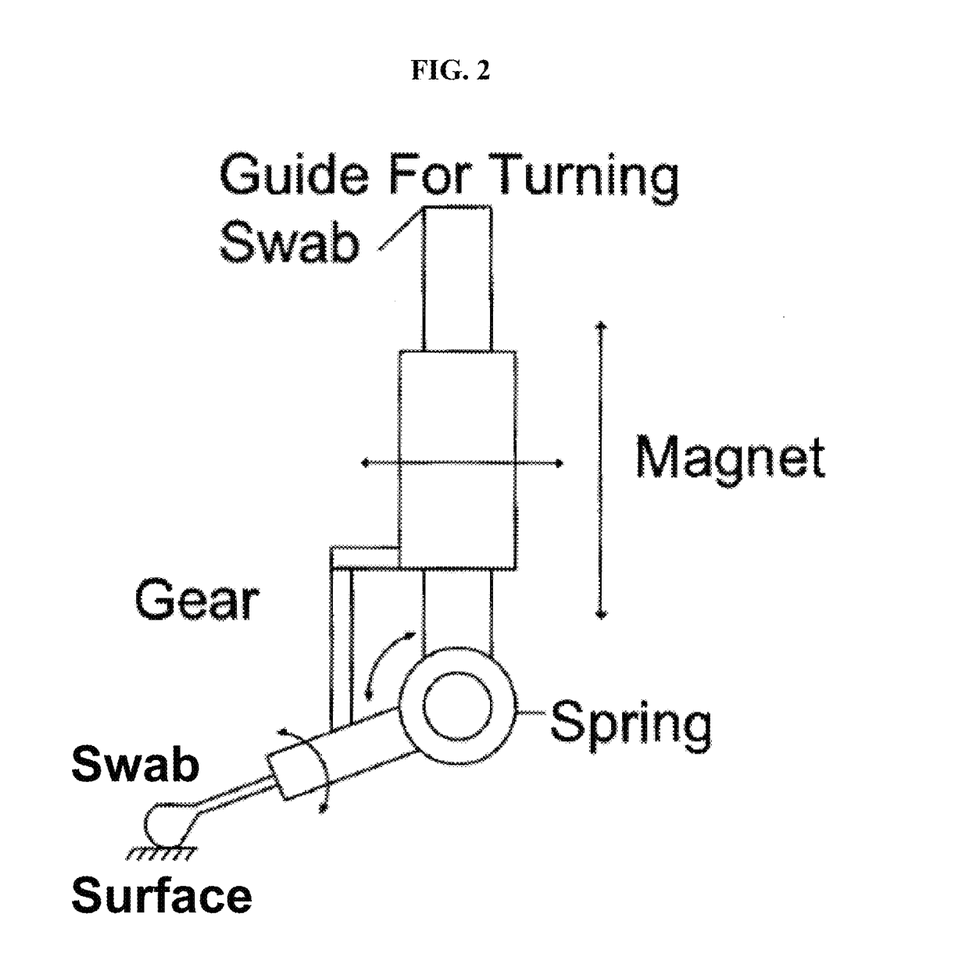
FIG. 2 is a schematic of an adjustable housing for the device of FIG. 1, according to some embodiments of the invention.
Figure 3:
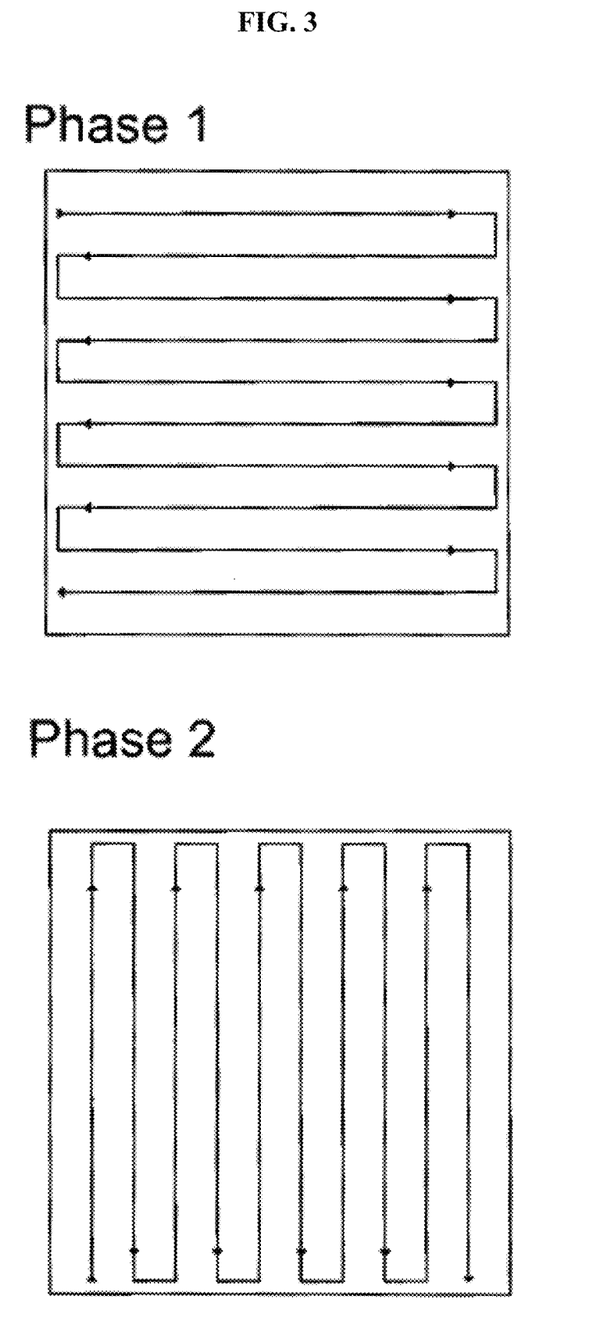
FIG. 3 is a depiction of an exemplary pre-defined two-phase swab pattern, in some embodiments.

An automatic cleaning validation swabbing device, in some embodiments of the invention, is an electro-mechanical device that moves a dry or wetted swab over a cleaned surface to recover any remaining soil left over from the cleaning process (see FIGS. 1 and 2).

The device is able to accept a standard sampling swab that has been optionally wetted with the required liquid solution (e.g., water or a suitable solvent). Preferably the swab is held at an angle to the surface being sampled. The swab should have constant pressure to ensure maximum recovery of soil or contaminants.

The device moves the swab head, which is in contact with the cleaned surface, over a pre-defined pattern. The device should control the swab head over the entire pattern, without requiring manual intervention. The total area sampled during the pattern may be 4 square inches, or any other area as may be desired or required according to certain protocols.

The swabbing pattern may be made up of two phases, such as depicted in FIGS. 3A and 3B. In some embodiments, the first phase requires that the swab head moves across the square pattern while maintaining the swab head orientation and constant pressure. The second phase in these embodiments requires the device to rotate the swab head 180 degrees before moving the swab head up and down the same square pattern while maintaining the swab head orientation and constant pressure. In other embodiments, the swab is moved in only one direction and is lifted between swabbing, e.g. in multiple straight lines or diagonal lines.

The device in some embodiments will allow for personnel to install and remove the swab without contacting the swab tip, to ensure accurate testing. In some embodiments, the device is capable of handling swabs with different shaft sizes (diameter and length) as well as swab tip.

The device may be made of off-the-shelf components with a number of items, such as the gears and guides. All outside (visible) surfaces may be made either from stainless steel or an acceptable gasket material (which, for example, may meet U.S. Food and Drug Administration requirements for the industry, if any). Any indicators used may be simple and off-the-shelf type components. In some embodiments, the device may be further customized and refined depending on the specific application to have more sophisticated components with added functionalities.

A benefit of this invention is to ensure swabbing consistency. This is achieved by a device that, among other things, maintains a consistent pressure between the swab and surface being sampled. In addition, the device of FIG. 1 ensures that the sample area is always a defined area, such as 4 square inches (defined by the outer frame).

In the prior art, an individual moves a wetted swab over a surface to recover soils that may still be on the surface after cleaning. Some individuals use a template to define a 4 square inch area for the sampling, but most just estimate the size of the area by sight. This technique is hard to perform when sampling vessels or tanks since the person executing the procedure can be far away from the sampling location or they must enter the vessel, which is costly and dangerous.

The device according to some embodiments may be placed on an extension arm and positioned inside the tank from the vessel manway. The device can operate effectively on curved surfaces and maintain correct contact with the surface.

Many variations of this invention are possible, as will be recognized by a person skilled in the art. In some embodiments, an adjustable pole may allow for the device to be placed inside confined spaces without personnel entry. In some embodiments, cameras and/or laser devices may be incorporated to guide the device to the correct location. In certain embodiments, the device is configured with an internal power supply (re-chargeable).

The device may be kept clean so that little or no residue is left on the surface being tested (swabbed). In some embodiments, the device may be configured with disposable covers to protect surfaces.

All publications, patents, and patent applications cited in this specification are incorporated herein by reference in their entirety as if each publication, patent, or patent application was specifically and individually put forth herein.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent that there are variations of the invention, which are within the spirit of the disclosure or equivalent to the inventions found in the appended claims, it is the intent that this patent will cover those variations as well. The present invention shall only be limited by what is claimed.

EXAMPLE

An exemplary method of the invention is as follows. Note that not all of these steps are practiced in some embodiments, and many variations are possible.

Figure 4:
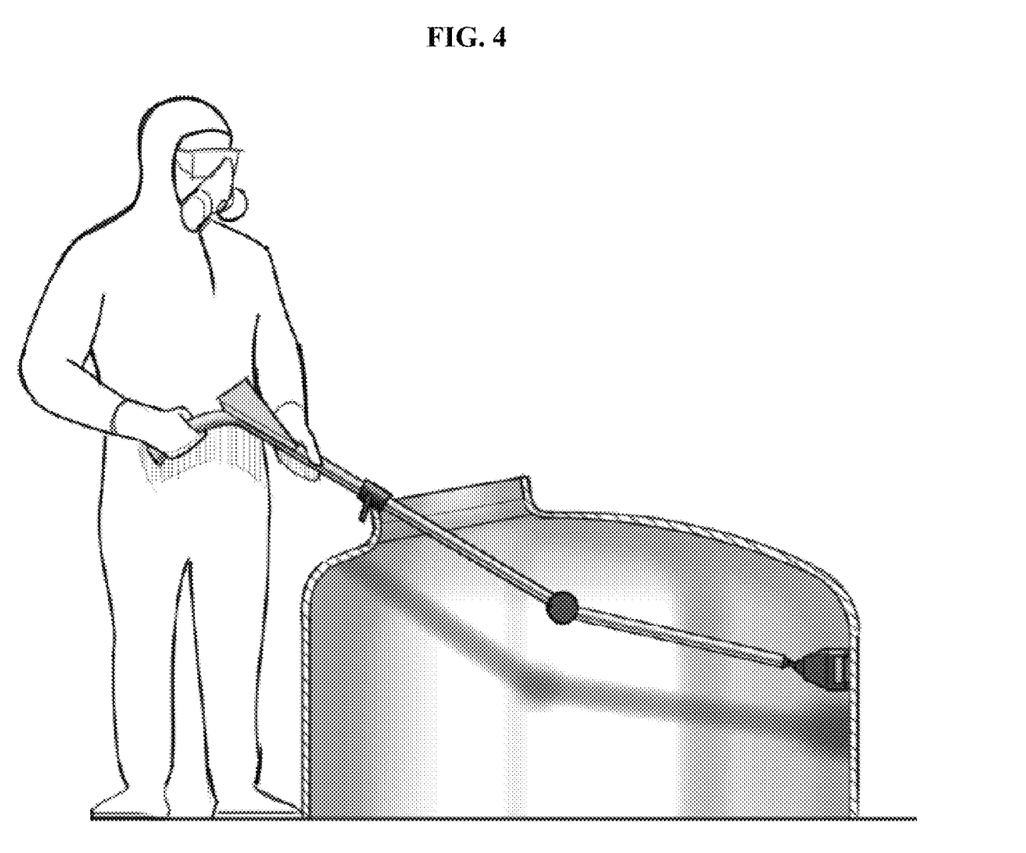
FIG. 4 depicts a user finding a tank wall so that it can be swabbed with a device, in some embodiments with an extension arm attached to the device.
Figure 5:
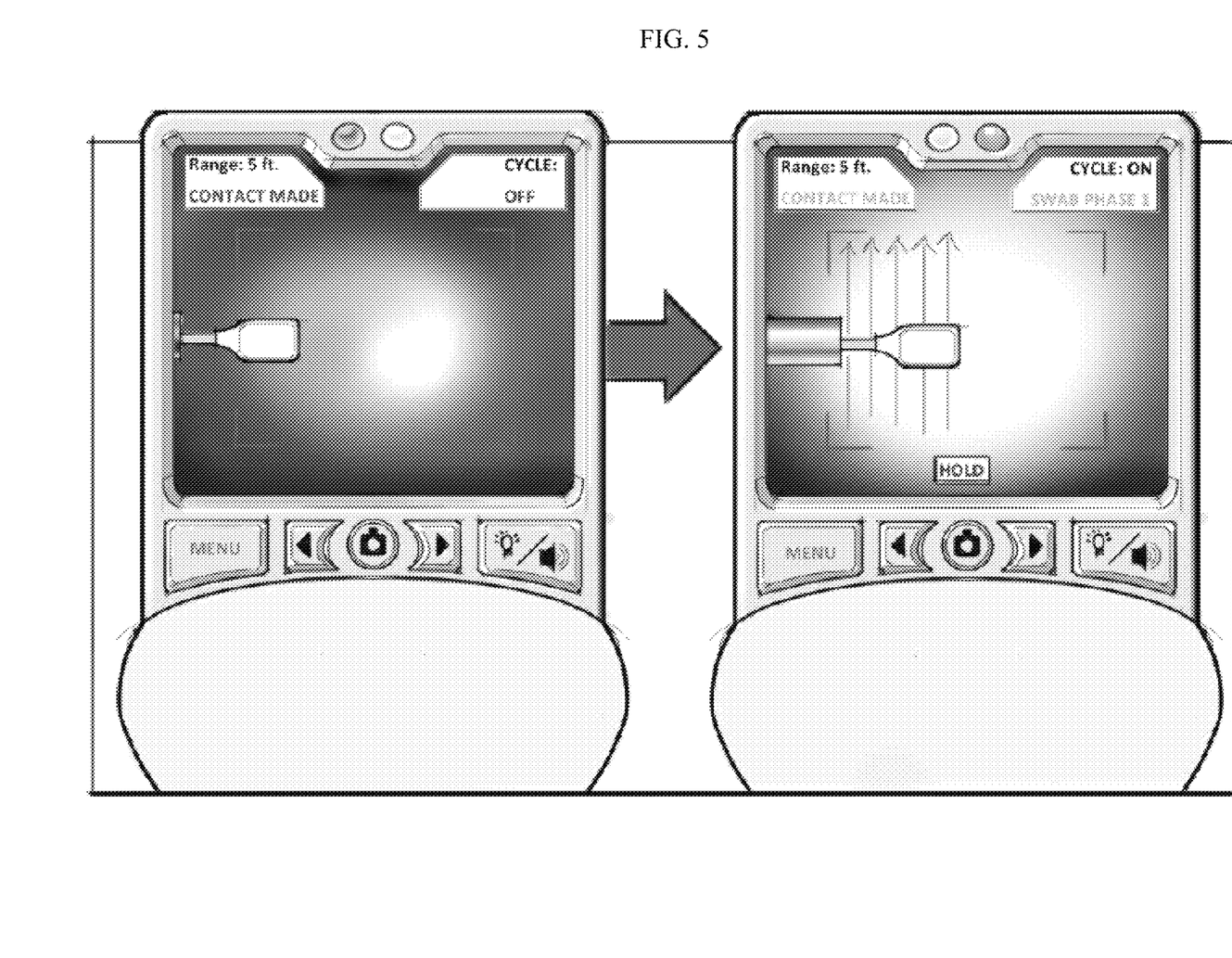
FIG. 5 depicts an exemplary GUI that aids a user to locate a tank wall for swabbing, in some embodiments.
Figure 6:
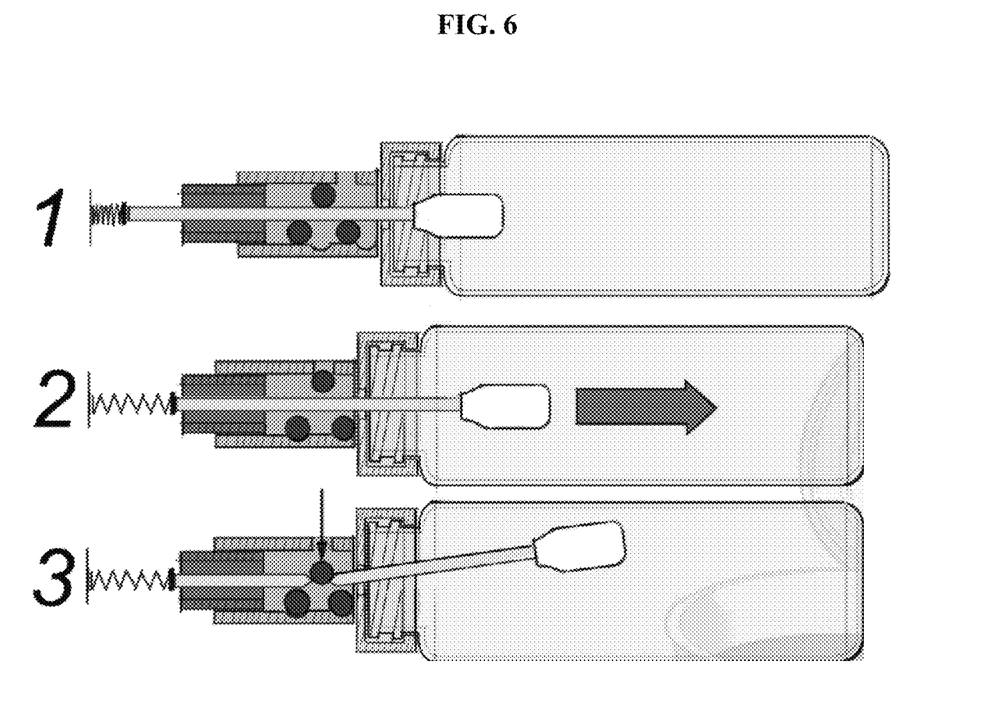
FIG. 6 illustrates a step of breaking off and ejecting a swab tip, in some embodiments of the invention.

Step 1. User transports device to tank.
Step 2. User frees validation device from storage mode.
Step 3. Validation device rotates around.
Step 4. Validation device stays up at accessible angle.
Step 5. While the device is hands-free a swab can be taken out.
Step 6. Swab is handled carefully.
Step 7. Box (with swabs) gets shut.
Step 8. Swab is inserted into device. This action may be automatic. For example, rollers or other means may be employed to draw in a swab.
Step 9. Disposable protective guard is installed on front of device.
Step 10. User unlocks manway.
Step 11. User opens up manway.
Step 12. Validation device is inserted through manway.
Step 13. User conducts visual inspection and finds tank wall through a graphical user interface (GUI). FIG. 4 depicts the user finding the tank wall, and FIG. 5 depicts an exemplary GUI. Optionally, lasers or other visual guides may be employed to assist in this step.
Step 14. Hook supports validation device along tank rim.
Step 15. Device moves swab over defined 2×2 in. area. Device moves swab along vertical axis in its first phase. On completion of phase 1, device rotates 90 degrees while swab is flipped 180 degrees. Device completes its last phase by swabbing along the horizontal axis.
Step 16. Device is pulled out of manway when validation test is complete.
Step 17. User secures device onto the stand.
Step 18. User removes protective cover.
Step 19. Swab is sent to "home" position so it is accessible.
Step 20. Container is screwed on to device to break off and eject swab tip. FIG. 6 illustrates this step.
Step 21. User lowers container and swab.
Step 22. User screws on cap.
Step 23. Device is put back into storage mode.
Step 24. User activates sterilization cycle on stand.

What is claimed is:

1. An automated method of cleaning validation of a selected surface, said method comprising:
   (a) selecting a sampling area contained within a selected surface to be validated for proper cleaning;
   (b) disposing an automatic cleaning validation swabbing electro-mechanical device onto said sampling area, wherein said automatic cleaning validation swabbing electro-mechanical device comprises an adjustable housing configured with an automatically movable and rotatable dry or wetted swab, wherein said swab is automatically movable and rotatable with an electronic controller, and wherein said swab is automatically inserted into said automatic cleaning validation swabbing electro-mechanical device;
   (c) using said automatic cleaning validation swabbing electro-mechanical device, moving said swab over said sampling area to recover residual contaminants, wherein said swab is moved over a pre-defined pattern within said sampling area using an electronic controller programmed to move said swab over said pre-defined pattern within said sampling area, wherein said pre-defined pattern includes two sequential patterns defining a first phase of movement and a second phase of movement of said swab, wherein said first phase of movement of said swab is perpendicular to said second phase of movement of said swab;
   (d) ejecting said swab into a container attached to said automatic cleaning validation swabbing electro-mechanical device, to ensure accurate testing;
   (e) measuring or testing said residual contaminants recovered during step (c); and
   (f) based on measurements or tests obtained in step (e), indicating whether or not said selected surface was properly cleaned prior to step (a).

2. The method of claim 1, wherein said selected sampling area is from 1 square inch to 10 square inches.

3. The method of claim 1, wherein said adjustable housing is configured to maintain a substantially constant surface pressure of said swab, to ensure swabbing consistency.

4. The method of claim 1, said method further comprising extending said automatic cleaning validation swabbing electro-mechanical device with an extension arm, whereby a human does not need to enter a vessel, reactor, or pipe.

* * * * *